United States Patent [19]
Knott et al.

[11] Patent Number: 5,899,918
[45] Date of Patent: May 4, 1999

[54] ANATOMICALLY CONFORMING EXTERNAL COMPRESSION DEVICE, NEW USE OF EXISTING NOSECLIP DEVICE, AND METHOD OF EXCLUSIVELY EXTERNAL NASAL COMPRESSION, FOR TREATING ANTERIOR NOSEBLEEDS

[76] Inventors: Michael McFarland Knott; Kyle Carmichael Knott, both of P.O. Box 5577, 355 Rose Pine Ct., Tahoe City, Calif. 96145

[21] Appl. No.: 09/012,411

[22] Filed: Jan. 23, 1998

[51] Int. Cl.$^6$ ............................................ A61B 17/04
[52] U.S. Cl. ................................................ 606/204
[58] Field of Search ........................ 606/204, 204.45, 606/157; 604/1, 286, 285; 24/545

[56] References Cited

U.S. PATENT DOCUMENTS

| | | |
|---|---|---|
| 4,457,756 | 7/1984 | Kern . |
| 5,464,413 | 11/1995 | Siska, Jr. et al. ........................ 606/151 |
| 5,662,679 | 9/1997 | Voss et al. ............................... 606/204 |

OTHER PUBLICATIONS

Barkin, Roger M., M.D. Pediatric Emergency Medicine: Concepts and Clinical Practice. Copyright 1992. pp. 646–650. Mosby Year Book, St. Louis, United States.

Hunt, Michael D. The Clinical Practice of Emergency Medicine. Copyright 1996. Second Edition, pp. 93–97. Lippincott–Raven, Philadelphia, United States.

Rosen, Peter., M.D. Emergency Medicine: Concepts and Clinical Practice. Copyright 1992. vol. 3, pp. 2465–2468. Mosby Year Book, St. Louis, United States.

Rosen, Peter., M.D. Essentials of Emergency Medicine. Copyright 1991. p. 551. Mosby Year Book, St. Louis, United States.

Strange Gary R., M.D. Pediatric Emergency Medicine: A Comprehensive Study. Copyright 1996. pp. 406–410. McGraw–Hill, New York, United States.

Tintinalli, Judith E., M.D. Emergency Medicine: A Comprehensive Study Guide. Copyright 1996. Fourth Edition, pp. 1083–1093. McGraw–Hill, New York, United States.

*Primary Examiner*—Michael Buiz
*Assistant Examiner*—Vikki Trinh
*Attorney, Agent, or Firm*—Hugh L. Holt

[57] ABSTRACT

This invention relates to external, non-invasive compression devices to treat anterior nosebleeds and a method for using those external compression devices to treat anterior nosebleeds without the insertion of any material or device into the nasal cavity. This patent concerns a method for automatically applying external pressure to the nose to stop nosebleeds, describes how a new use can be made of an existing device to implement the method, and also describes a preferable anatomically conforming device which better fits the shape of the nose and thus can be more comfortable and effective.

5 Claims, 4 Drawing Sheets

ANATOMICALLY CONFORMING EXTERNAL COMPRESSION DEVICE, NEW USE OF EXISTING NOSECLIP DEVICE, AND METHOD OF EXCLUSIVELY EXTERNAL NASAL COMPRESSION, FOR TREATING ANTERIOR NOSEBLEEDS

BACKGROUND OF THE INVENTION

A. FIELD OF THE INVENTION

This invention relates to devices that apply external, non-invasive, compression to treat nosebleeds and a method for using those external compression devices to treat anterior nosebleeds.

B. DESCRIPTION OF PRIOR ART

1.) Treatment of Nosebleeds

Nosebleeds may occur in the anterior (front) or posterior (back) area of the nasal passage. The treatment of posterior nosebleeds is exclusively internal and invasive, and is usually done in the emergency room or operating room by a physician specializing in the treatment of ear, nose and throat problems.

Anterior nosebleeds are usually treated at home and only 8 to 10% are serious or recurrent enough to require professional medical attention. The treatment of anterior nosebleeds can be divided into two methods: (a) internal or invasive methods, and (b) external or non-invasive methods.

a.) Internal Treatment

Internal treatment of anterior nosebleeds includes the use of three primary methods: vasoconstricting drugs, cautery, and insertion of various materials or devices to expedite clotting.

i.) The first internal treatment method is the use of vasoconstriction drugs instilled by spray bottle, atomizer, cotton pledget, or internal nosebleed clip. Vasoconstriction compounds include phenylephrine, oxymetozaline, epinephrine or cocaine, which act by causing the blood vessels in the nose to decrease in diameter and thus reduce blood flow. Kern (U.S. Pat. No. 4,457,756) disclosed an internal nosebleed clip with cotton pads that can be saturated with a vasoconstricting agent and inserted into the nostril(s). The clip exerts gentle pressure from inside the nose which can be augmented by finger pressure on the external portions of the clip or on the external surfaces of the tip of the nose.

ii.) The second internal treatment method is the use of cautery, which is the process of burning, and can be effected by chemical, electrical, or thermal means. Chemical cautery involves the touching of the bleeding site with silver nitrate sticks for 10 to 15 seconds. This treatment cannot stop bleeding, but is applied only after the bleeding has stopped to prevent re-bleeding. Overzealous use has caused septal perforations. Electrical cautery uses electrical energy to coagulate the bleeding area and is used almost exclusively by ear, nose and throat specialists. Thermal cautery uses a battery powered disposable device but it is difficult to control or estimate the depth of cautery achieved with these devices. Serious damage to the delicate nasal tissues can occur.

iii.) The third internal treatment method is insertion of various materials and devices into the nasal cavity to expedite clotting. All existing techniques involve the insertion of materials or other devices into the nasal cavity and the application of pressure either internal or external to stop bleeding. The materials used include petroleum-impregnated gauze, absorbent-cotton gauze, synthetic sponge, balloon devices, and thrombogenic agents. Pressure may be applied internally-specifically, by inserting a sufficient amount of packing material to apply pressure itself, by expansion of the sponge material when it contacts nasal fluids, by inflation of a balloon or, pressure may be applied externally, to cause an internal material to contact the bleeding nasal surfaces. These internal methods may use pressure alone or may be combined with an agent such as absorbent-cotton or thrombogenic chemical to expedite clotting. Absorbent-cotton has fine fibers that hold liquid blood adjacent to the bleeding vessel until a clot is formed thereby stopping bleeding. Thrombogenic chemicals also act to promoting clotting by enhancing the conversion of fibrinogen to fibrin.

Baer (U.S. Pat. No. 3,349,771) used absorbent-cotton placed inside the nose and a nasal clamp placed on the outside of the nose to force the bleeding areas of the nose into tight contact with the absorbent-cotton. Kern used an internal nosebleed clip to deliver vasoconstricting agents directly to the nasal mucosa. Neither of these internal treatment methods were widely adopted, as they still required insertion of material into the nasal cavity, with the attendant problems and risks of such internal treatment discussed herein.

Insertion of petroleum-impregnated gauze or absorbent-cotton is also painful and requires subsequent removal that may restart bleeding. Furthermore, it is difficult for internal packing to be inserted with sufficient uniformity to apply constant and evenly distributed pressure to the entire anterior nasal septum. There are many commercial products that have been designed to make the pressure more uniform, the insertion faster, more convenient and less uncomfortable for the patients. For example, the Merocel® (a product and trademark of the Merocel Corp., Mystic, Conn.) nasal sponge is a dehydrated, synthetic sponge-like material that expands upon contact with moisture. In addition, balloon devices can be inserted into the nasal cavity and inflated with air.

All of the above internal treatment methods, because of their inherent invasive nature, suffer from the disadvantages of causing the patient to suffer discomfort, possibly injuring the delicate nasal tissues, and in many cases requiring the services of a trained medical professional. Even with these disadvantages, the internal techniques are still not as effective as applying external pressure alone directly to the external nose.

b.) External Treatment

As opposed to internal treatment methods, exclusively external treatment is non-invasive and involves the application of pressure to the outside of the nose. External treatment of nosebleeds is the most effective way to apply pressure to the blood vessels in the nasal septum. Traditionally, the recommended technique is to have the patient use his own hand to apply pressure to the entire elastic area of the nose, using what is referred to as the "closed hand technique." To do so, the radial aspect of the index finger between the proximal and distal interphalangeal joints rests against the side of the nose and the thumb is used to exert pressure to the opposite side of the nose. The patient's arm and elbow are rested on the chest to help maintain the proper position. This technique is recommended because it reduces the risk that the patient will loosen his or her grip. A watch or clock should confirm the duration of compression for 5 to 10 minutes because patients invariably underestimate the amount of time that has elapsed.

In simple terms the nose is pinched between the thumb and index finger for 5 to 10 minutes. If properly and consistently applied for the recommended duration, this method can be effective for treating simple anterior nosebleeds. However, in practice its effectiveness is diminished because of the difficulty in maintaining constant pressure for even the minimum time period required (5 minutes). It is especially problematic in children because it must be done by the parent or other adult.

There are no known devices presently available that are designed to treat nosebleeds solely by the application of external pressure to the nose, which is an object of this invention.

2.) The Existing Use of a Noseclip Devices

An existing noseclip devices apply external compression to effect closure of the nostrils for the purposes of preventing water from entering the nostrils during swimming, performing respiratory function testing and delivering breathing treatments. Swimming noseclips pinch the inferior aspect of the nose to cause closure of the nostrils thus preventing the entry of water. In its existing respiratory use the noseclip is placed on the nose for the purpose of stopping the flow of air through the nasal passages. This closure causes air to move only through the mouth. Thereby, all the breathing air moves from the lungs through the mouth to an external respiratory measuring machine (respirometer) or breathing machine. This allows accurate measurement of lung volumes and flow or delivery of air, oxygen and/or medication.

Swimming noseclips are plastic U-shaped devices that are placed on the nose usually from the inferior aspect. Commercial noseclips are available (Swimline Nose Pinch, Edgewood, N.Y. and Future Way Corp., Floral Park, N.Y.). Existing respiratory noseclips are made of flexible plastic in the shape of a clothespin, and typically include some type of "pad" on the end of the inside surface that contacts the nose in order to reduce patient discomfort and enlarge the area of compression. Soft plastic, rubber, foam, sponge, or other soft materials are used to form the pads. There are numerous commercially available respiratory noseclips (Warren E. Collins, Inc., Braintree, Mass.; Vacumed, Ventura, Calif.; A-M System, Inc., Everett, Wash.) which vary in their shape and pad design (FIGS. 1A, 1B, 1C). The device is operated by squeezing the upper connecting arms 10 (FIG. 1C) between the thumb and first finger with force 11 sufficient to causes the lower connecting arms 12 to open 13 sufficiently wide to be placed on the nose.

C. The Problem

Nosebleeds occur in both adults and children, but are especially common in children. There is a need for a non-invasive treatment for this problem that is effective and yet safer than internal, invasive methods, and that can and will be administered by the patient or, if the patient is a child, by the child's parent, without the need for trained medical personnel. The invention must deliver uniform pressure to the entire soft portions of the external nose rather than just pinch the inferior aspect as with the swimmers noseclip. The invention described herein is designed to fulfill these needs. The inventor is an emergency medicine physician who has developed a new use of the existing respiratory noseclip device, a method for use of an external compression device to treat nosebleeds, and who has designed an anatomically conforming device to more effectively and comfortably provide such compression, all as described in this patent.

Ten percent of the American population has had at least one or more episodes of nosebleeds. Most of these are in children. Common causes of nosebleeds in children include picking the nose, nasal dryness, and minor trauma. The bleeding soils clothing, bedding, and furniture and is inconvenient. For the parents and children, bleeding represents a distressing occurrence.

In adults there is a small (and in children a very rare) but important percentage of nosebleeds which are located in the back (posterior) portions of the nasal passage and are serious, requiring urgent medical attention. The external compression device and method described in this patent are not for use in such patients.

Internal treatment of nosebleeds is invasive, painful, and usually requires medical professionals. Parents are generally unwilling to insert anything into their child's nose because of their concern over the discomfort it causes and the not unreasonable fear of injury to the child. Even adults are reluctant to insert these devices into their own noses for the same reasons and because it is difficult to self-administer objects such as a dry sponge, gauze, or internal clip into the sensitive nasal mucosa.

The existing closed hand (finger-thumb) method of external treatment of nosebleeds requires uniform pressure delivered continuously by hand for 5 to 10 minutes to an adult or child. This method is difficult to apply and tiring in practice, although if properly applied it can be effective.

D. The Object

The object of this invention is to provide an effective, safe, painless, non-invasive, exclusively external device, and a method for using such a device, which automatically delivers continuous, uniform pressure to the entire pliable lateral aspect of the lateral walls of the nose to treat simple anterior nosebleeds, without the need for treatment by trained medical personnel. This treatment can place pressure directly on the bleeding vessel, thereby typically causing cessation of the flow of blood and allowing the body's normal coagulation process to control the bleeding. This treatment can be accomplished with the use of the existing respiratory noseclip or, preferably, the new anatomically conforming noseclip described herein.

SUMMARY OF THE INVENTION

The invention is (1) a new device, that is, an external compression device that anatomically conforms to the shape of the nose, and (2) the method of using an external compression device, including the existing device and the new device, to treat simple anterior nosebleeds without the insertion of any material or device into the nasal passage. A pre-existing nose compression device previously used for other purposes can be utilized in a new use of that device as described herein, or preferably, the new anatomically conforming device that is a subject of this patent can be used. In either case, this is a new method of controlling nosebleeds by using an external compression device alone, which, after being applied to the external nose, automatically applies pressure to the external nose for sufficient time to allow the body's normal coagulation mechanism typically to stop the flow of blood by forming clotted blood within the lumen of the bleeding vessels. The method and device have the advantages of being effective, easy to apply by persons without medical training, and of not requiring the insertion of any uncomfortable or potentially injurious device, mechanism, substance, material or instrument into the internal nostril or nasal cavity.

DESCRIPTION OF THE PREFERRED EMBODIMENT

Figure 1A:
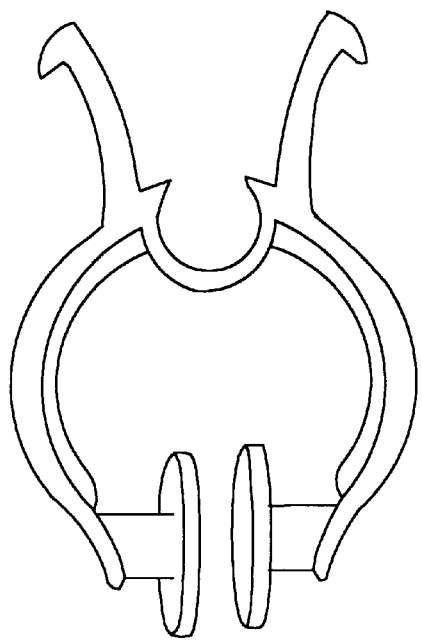
FIGS. 1A, 1B, 1C are front views showing commercially available noseclips.
Figure 1B:
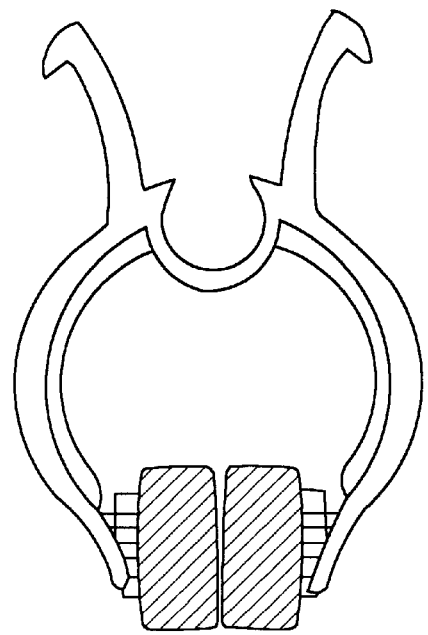
Figure 1C:
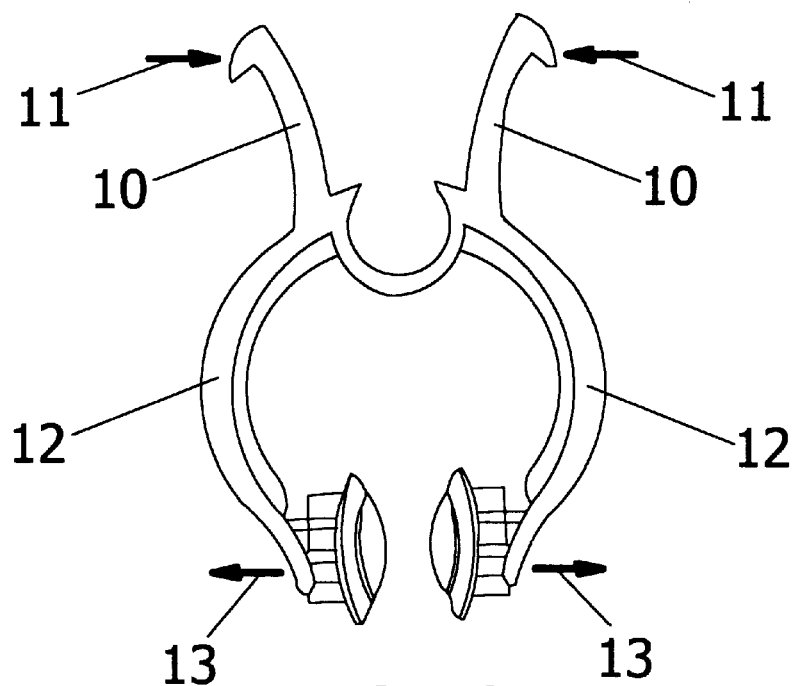
Figure 2:
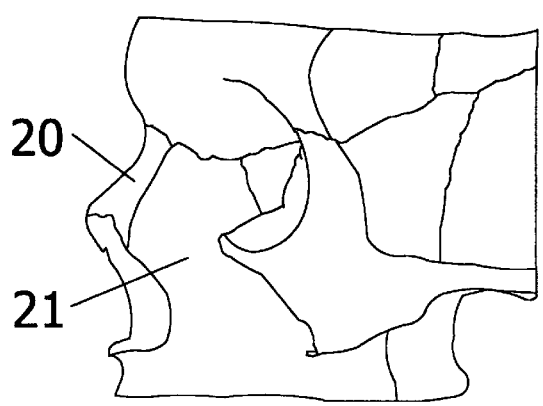
FIG. 2 is a side view of the skull showing bones of the face.
Figure 3:
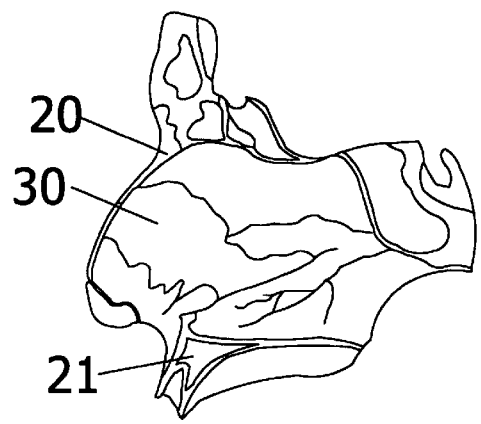
FIG. 3 is a midline view showing cartilage of the septum and nasal bones.

Referring FIG. 2, the bony structure of the face is shown. The nasal bone 20 joins the maxilla 21 inferior and posterior. These two bones adjoin the pliable cartilage of the septum 30 and lateral walls (removed) of the nose as shown in FIG. 3.

Figure 4:
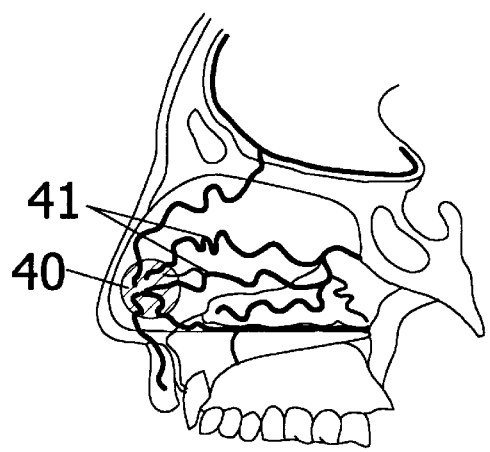
FIG. 4 is a midline view of the anterior nasal cavity showing blood vessels associated with the most common site of anterior nosebleeds.
Figure 5:
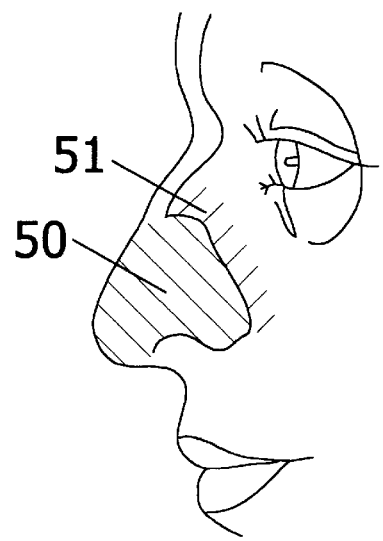
FIG. 5 is a side view of the face showing soft and hard bony parts of the nose.

FIG. 4 shows the superficial blood vessels of the septum located in the Little's area 40 which is the anterior portion of Kisselbach's plexus 41 and is the most common site of anterior nosebleeds. Because these blood vessels are located in the soft pliable region of the nose, they can be compressed by applying a device to this soft region of the nose 50 (FIG. 5). The uncompressible bony area 51 is shown in FIG. 5. This soft area 50 is the preferred area for placement 60 and 61 of the device and is shown in FIG. 6A.

Figure 6A:
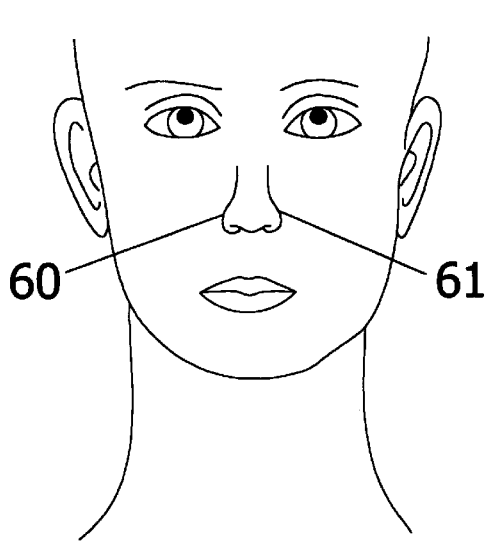
FIGS. 6A, 6B are front views of the face showing the general placement of and the direction of force supplied by the external compression device.
Figure 6B:
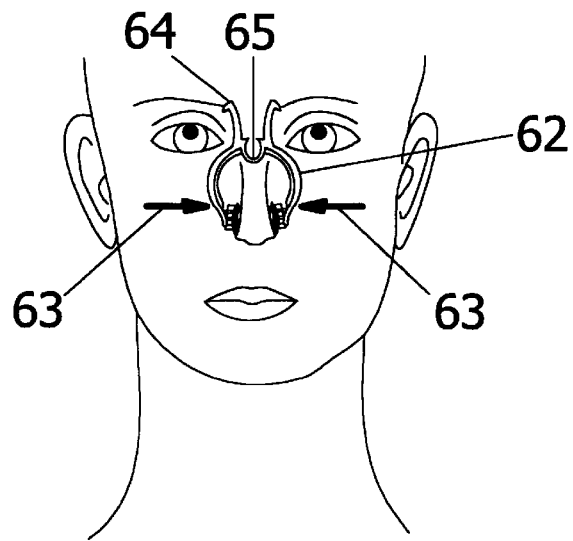

The device is placed on the right 60 and left 61 lateral walls (sides) of the external nose (FIG. 6A). As shown in FIG. 6B, the device 62 has force 63 sufficient (0.5 to 2 psi) to cause these pliable structures to move medially toward and come into direct opposition with the midline structure, the nasal septum. The force 63 supplied by the device mechanism brings the lateral walls and the septum into direct contact and causes collapse and compression of the blood vessels in the nasal septum and lateral walls. This compression force is sufficient to cause cessation of the leakage of blood from those vessels. The external compression device is left on the nose for time sufficient (5 to 10 minutes) to allow the body's normal coagulation mechanism to activate and form coagulated blood, which continues to occlude the blood vessel lumen when the device is removed. The resultant effect of this method and use of a device is typically to stop the nosebleed.

Figure 7:
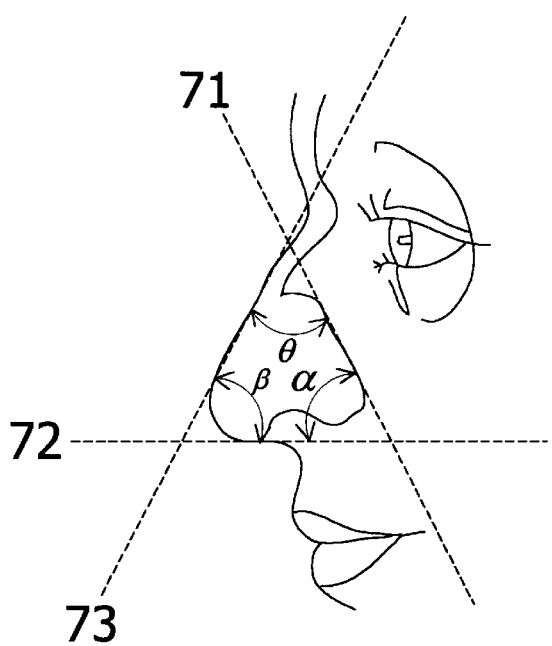
FIG. 7 is a side view of the face showing the approximate angles of the anatomically conforming pad compression area.

In FIG. 7 axis 71 follows the inferior border of the nasal and maxillary bones, which adjoin and are contiguous with the lateral and alar nasal cartilages. Axis 72 begins at its most posterior extent at the anterior border of the maxilla and extends through the inferior-most border of the external nose. Axis 73 follows the anterior and superior border of the external nose as viewed laterally. Angle α is formed by the intersection of axis 71 and axis 72 and is 72°±5°. Angle β is formed by the intersection of axis 72 and axis 73 and is 50°±5°. Angle θ is formed by the intersection of axis 71 and axis 73 and is 58°±5°.

Figure 8:
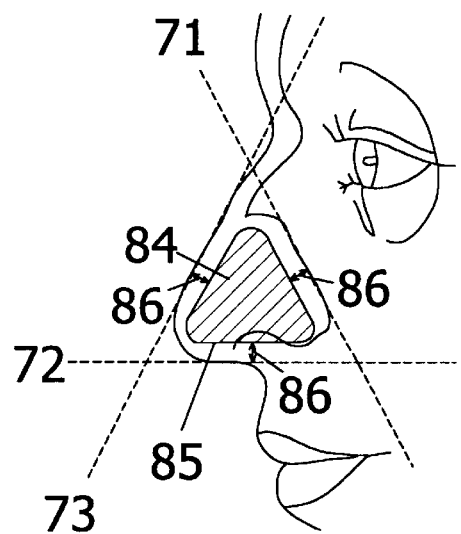
FIG. 8 is a side view of the face showing the pad compression area of the adult anatomically conforming noseclip pad.

In FIG. 8, the area of compression 84 is the portion of the nose inset 0.2 to 0.5 cm (86) and parallel to the lines making up the triangle formed by axis 71, axis 72, and axis 73, In the adult, each side 85 of the compression triangle 84 is approximately 2.0 cm±0.6 cm (FIG. 8). In the pediatric or small adult, each side 85 of the compression triangle 84 is approximately 1.4 cm±0.4 cm.

Figure 9:
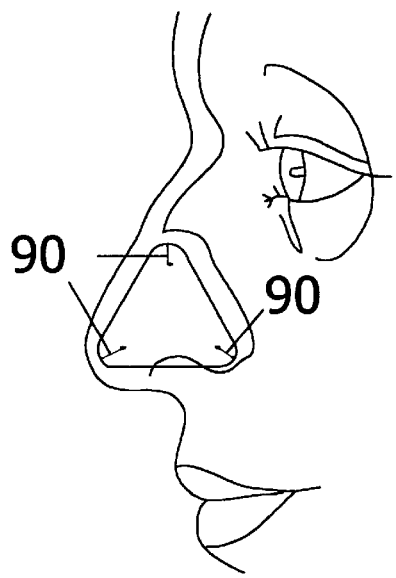
FIG. 9 is a side view of the face showing the arc radii of the rounded triangular anatomically conforming pad compression area.
Figure 10:
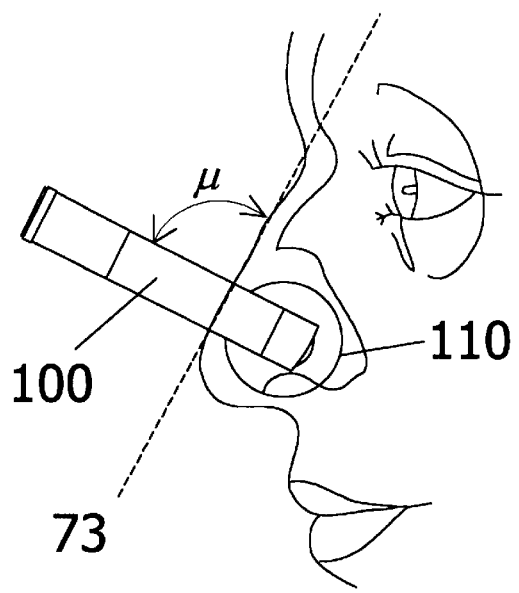
FIG. 10 is a side view of the face showing the location and angle of attachment of the noseclip arms to the existing noseclip pad.
Figure 11:
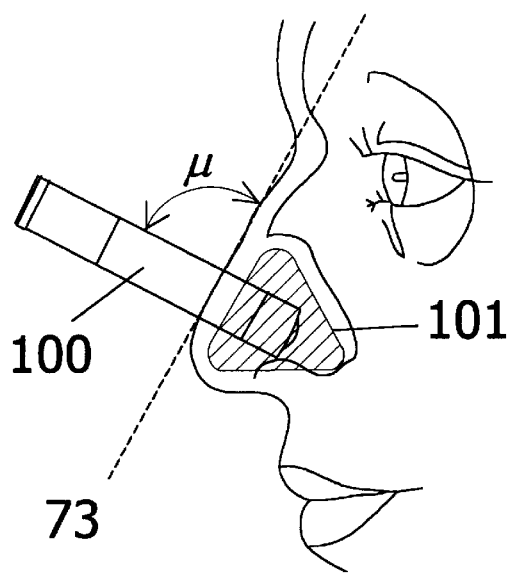
FIG. 11 is a side view of the face showing the location and angle of attachment of the noseclip arms to the anatomically conforming pad.

The compression area 84 is inset from the outer borders of the triangular shape of the nose to avoid the thicker and less compressible superior and inferior edges of the external nose and to avoid the area of cartilage adjoining the boundary of the anterior and inferior nasal and maxillary bones. This inset allows more uniform pressure to be applied to the lateral walls of the external nose, thereby transferring this uniform force (pressure) to the entire nasal septum. The triangular pads have rounded corners of an approximate arc-radius of 0.2 to 1.0 cm 90 (FIG. 9), the smaller end of the range applying to the pediatric or small adult. The arms 100 of the anatomically conforming noseclip are attached to the anatomically conforming pads 101 at an angle $\mu$ to axis 73. The arms 100 of the existing noseclip are also attached to the circular pads 110 at an angle $\mu$ to axis 73. Angle $\mu$ may range from 75° to 105° depending on the anatomical variation and size of the individual (FIGS. 10 and 11).

Operation of the Preferred Embodiment

The device 62 is opened manually by an individual pressing the upper connecting arms 64 FIG. 6B together and the device is placed on the soft part 50 of the external nose (FIGS. 5, 6A, and 6B). By pressing the upper connecting arms 64 together this opening pressure is stored as potential energy in the physical structure of the device. Specifically, the energy is stored by the semi-elastic material structure of the device as it is deformed from its resting and static shape; such energy is stored most significantly in the connecting bridge 65 between the bases of the upper connecting arms. When placed on the nose the opening pressure is released causing the device's stored potential energy to apply dynamic force 63 (FIG. 6B) adequate to move the lateral walls 60 and 61 (FIG. 6A) of the external nose in a medial direction such that the medial surface of the lateral walls become opposed to, into direct contact with, transmit and maintain the closing pressure of the device to, the lateral surfaces of the septum. By this method and process, the bleeding vessel(s) is (are) caused to collapse, thereby typically stopping the flow of blood from the bleeding vessel(s). The body's coagulation mechanism is then allowed to activate, forming clotted blood which occludes the vessel, thereby normally stopping further loss of liquid blood when the device is removed. In this manner, the nosebleed is controlled.

The device is placed on the nose such that the anatomically conforming triangular shape of the pad matches the soft compressible portions of the lateral walls of the nose. The force supplied by the device causes the lateral walls to move medially to contact the lateral surfaces of the septum and transfer the force to that structure. This process compresses the bleeding vessel(s) thereby causing a cessation of bleeding The anatomically conforming shape delivers the compressing force (pressure) 63 to a larger and more appropriate portion of the nasal septum.

We claim:

1. An exclusively external nasal compression device for the treatment of anterior nosebleeds, the device comprising:
    at least two arms, each having a proximal end and a distal end;

a connecting bridge which connects said at least two arms for allowing the distal ends of the arms to move together and apart respectively toward a released position and a squeezed position of the proximal ends, said connecting bridge has a curved shape;

pads, each attaching to said distal end of said arm, wherein said pad has an equilateral triangle shape to conform the anatomy of the soft pliable portions of the external nose, each side of said triangle having a length in a range from 1 cm to 2.6 cm; and whereby when placing the device onto the external portions of the nose and applying the distal ends in the released position of the proximal ends, the distal ends of the device exerts a force onto the lateral surfaces of the lateral walls of the soft cartilaginous structures of the external nose, the force is sufficient to effect the lateral walls to move medially and become opposed to and in direct contact with the lateral surfaces of the septum, thereby providing the formation of the clotted blood.

2. The external nasal compression device according to claim 1, wherein the connecting arm is attached to one side of the pads at an angle in a range from 30 degrees to 120 degrees relative to a connected edge of the pad.

3. A method for treating anterior nosebleeds solely by external means, the method comprising:

placing an external nasal compression device to a patient's nose, wherein the device includes at least two arms, each including a proximal end and a distal end, a bendable crossbeam which connects said at least two arms for allowing the distal ends of the arms to move together and apart toward a released position and a squeezed position, respectively, of the proximal ends, and pads, each attaching to said distal end of said arm, wherein said pad has a configuration to conform to the anatomy of the soft pliable portions of the external nose; and applying and maintaining a force with the distal ends of the device to the lateral surfaces of the lateral walls of the soft cartilaginous structures of the external nose adequate to cause the lateral walls to move medially and become opposed to and in direct contact with the lateral surfaces of the septum, thereby providing the formation of the clotted blood within the bleeding vessel in the lining of the septum and lateral walls.

4. The method as recited in claim 3, wherein said pad has an equilateral triangle, each side of said triangle having a length in a range from 1 cm to 2.6 cm.

5. The method as recited in claim 3, wherein said arm attaches to a side of said pad at an angle in a range from 30 degrees to 120 degrees relative to a connected edge of the pad.

* * * * *